US006821291B2

(12) United States Patent
Bolea et al.

(10) Patent No.: US 6,821,291 B2
(45) Date of Patent: Nov. 23, 2004

(54) RETRIEVABLE STENT AND METHOD OF USE THEREOF

(75) Inventors: Stephen L. Bolea, Watertown, MN (US); Robert L. Rykhus, Jr., Edina, MN (US); Sidney F. Hauschild, Brooklyn Park, MN (US); Johann J. Neisz, Coon Rapids, MN (US); Mark Polyak, Minnetonka, MN (US); Bradford G. Staehle, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 198 days.

(21) Appl. No.: 09/904,926

(22) Filed: Jul. 13, 2001

(65) Prior Publication Data

US 2002/0188344 A1 Dec. 12, 2002

Related U.S. Application Data

(60) Provisional application No. 60/295,128, filed on Jun. 1, 2001.

(51) Int. Cl.[7] .................................................. A61F 2/06
(52) U.S. Cl. ...................................... 623/1.11; 606/108
(58) Field of Search ............................... 623/1.11, 1.32, 623/1.33, 23.66, 23.7; 606/108, 191, 194, 198, 200; 604/93.01, 526

(56) References Cited

U.S. PATENT DOCUMENTS

| 4,553,545 A | 11/1985 | Maass et al. |
| 4,649,922 A | 3/1987 | Wiktor |
| 4,655,771 A | 4/1987 | Wallsten |
| 4,762,128 A | 8/1988 | Rosenbluth |
| 4,771,773 A | 9/1988 | Kropf |
| 4,800,882 A | 1/1989 | Gianturco |
| 4,893,623 A | 1/1990 | Rosenbluth |

(List continued on next page.)

FOREIGN PATENT DOCUMENTS

| EP | 829242 A1 | 5/1987 |
| WO | 92/11824 | 7/1992 |
| WO | 93/11719 | 6/1993 |
| WO | 94/20044 | 9/1994 |
| WO | 94/26174 | 11/1994 |
| WO | 95/05788 | 3/1995 |
| WO | 95/29646 | 11/1995 |
| WO | 96/26682 | 9/1996 |
| WO | 99/55245 | 11/1999 |
| WO | 00/00105 | 1/2000 |

*Primary Examiner*—Brian E. Pellegrino
(74) *Attorney, Agent, or Firm*—Kagan Binder, PLLC

(57) ABSTRACT

A removable stent system and method for extraction of a removable stent from a target site is disclosed. The removable stent includes a removable stent having a collapsible end and a collapsing element configured for coupling with a removal tool. The collapsing element can be configured as a lasso or can be movable between two positions when deployed at a target site in vivo. The removable stent overcomes disadvantages and limitations of previous types of stents as well as overcoming complications during or following stent deployment in vivo. The removable stent further includes features that increase its ease of use and reduce the maneuvering required of devices or tools used to remove the stent. This then decreases the amount of effort required by the physician, the procedure time, and the level of discomfort experienced by a patient during the procedure.

1 Claim, 16 Drawing Sheets

U.S. PATENT DOCUMENTS

| | | |
|---|---|---|
| 4,954,126 A | 9/1990 | Wallsten et al. |
| 4,990,151 A | 2/1991 | Wallsten |
| 5,026,377 A | 6/1991 | Burton et al. |
| 5,035,706 A * | 7/1991 | Gianturco et al. .......... 606/198 |
| 5,061,275 A | 10/1991 | Wallsten et al. |
| 5,078,720 A | 1/1992 | Burton et al. |
| 5,100,429 A | 3/1992 | Sinofsky et al. |
| 5,192,297 A | 3/1993 | Hull |
| 5,261,916 A | 11/1993 | Engelson |
| 5,330,482 A | 7/1994 | Gibbs et al. |
| 5,350,397 A | 9/1994 | Palerom et al. |
| 5,356,423 A | 10/1994 | Tihon et al. |
| 5,372,600 A | 12/1994 | Beyar et al. |
| 5,411,507 A | 5/1995 | Heckele |
| 5,464,408 A | 11/1995 | Duc |
| 5,474,563 A | 12/1995 | Myler et al. |
| 5,591,172 A | 1/1997 | Bachman et al. |
| 5,624,450 A | 4/1997 | Glastra |
| 5,643,309 A | 7/1997 | Myler et al. |
| 5,667,486 A | 9/1997 | Mikulich et al. |
| 5,700,269 A | 12/1997 | Pinchuk et al. |
| 5,702,419 A | 12/1997 | Berry et al. |
| 5,713,948 A | 2/1998 | Uflacker |
| 5,733,302 A | 3/1998 | Myler et al. |
| 5,749,921 A | 5/1998 | Lenker et al. |
| 5,759,186 A | 6/1998 | Bachmann et al. |
| 5,782,838 A | 7/1998 | Beyar et al. |
| 5,810,873 A | 9/1998 | Morales ..................... 606/198 |
| 5,814,062 A | 9/1998 | Sepetna et al. ............. 606/198 |
| 5,843,117 A | 12/1998 | Alt et al. ................ 606/108 X |
| 5,911,752 A | 6/1999 | Dustrude et al. ............ 623/1.1 |
| 5,941,895 A | 8/1999 | Myler et al. ............ 606/198 X |
| 5,954,729 A | 9/1999 | Bachmann et al. ......... 606/108 |
| 5,964,771 A | 10/1999 | Beyar et al. ................ 606/108 |
| 5,984,957 A | 11/1999 | Laptewicz, Jr. et al. |
| 6,019,779 A | 2/2000 | Thorud et al. |
| 6,132,458 A | 10/2000 | Staehle et al. |
| 6,143,021 A | 11/2000 | Staehle et al. |
| 6,149,680 A | 11/2000 | Shelso et al. |
| 6,183,504 B1 | 2/2001 | Inone |
| 6,235,054 B1 | 5/2001 | Berg et al. |
| 6,245,103 B1 | 6/2001 | Stinson |

* cited by examiner

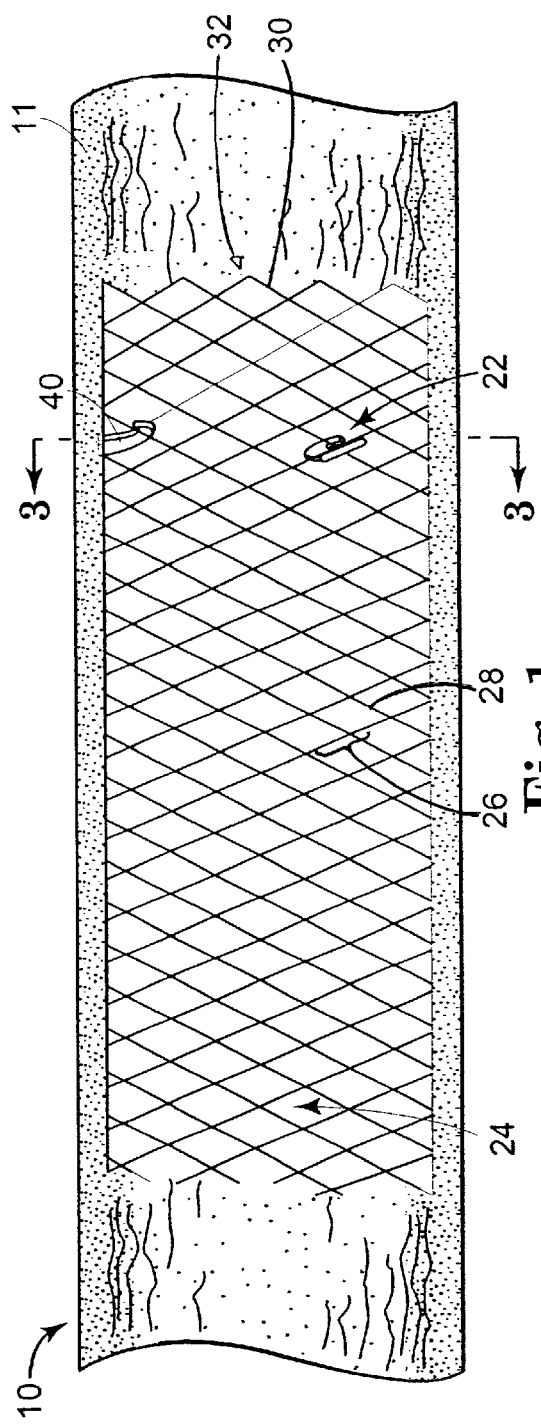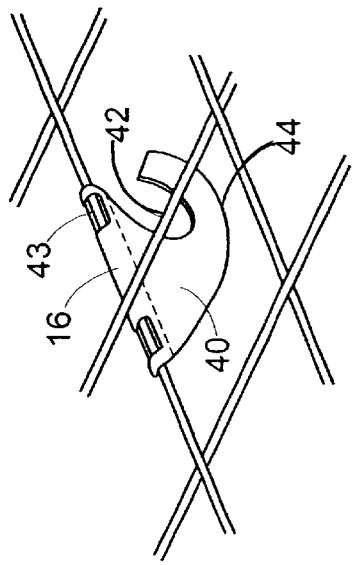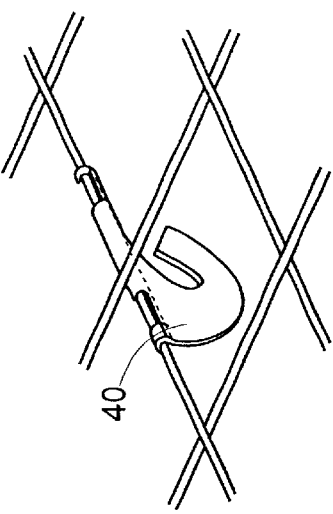

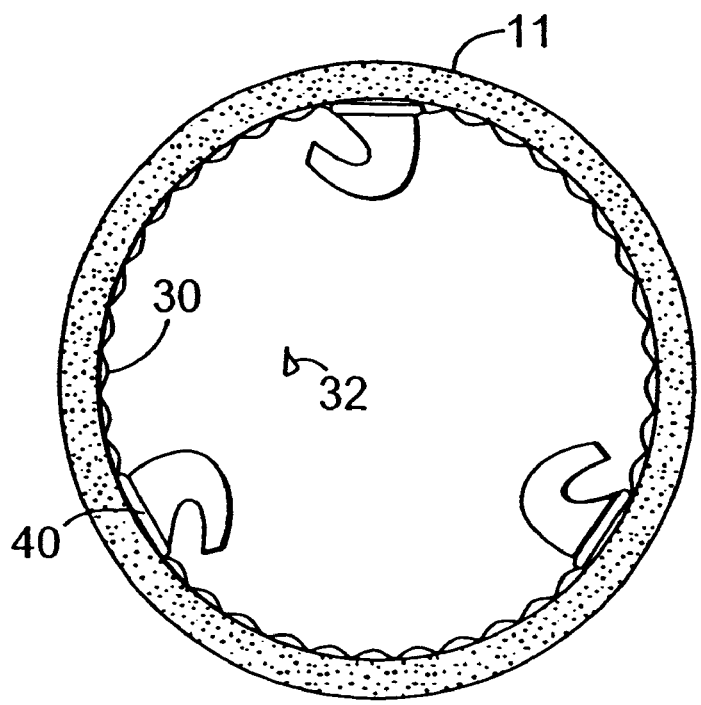
Fig. 3
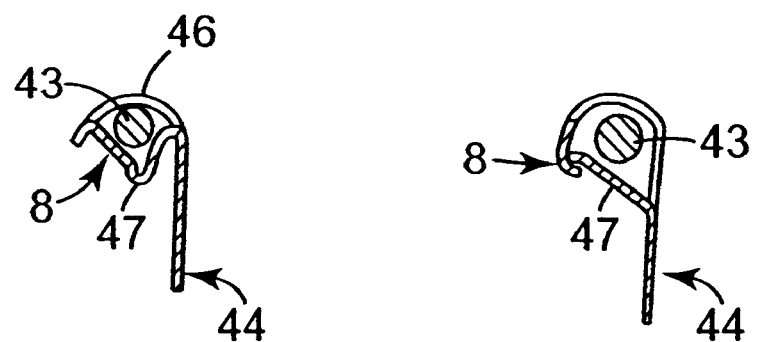
Fig. 4A       Fig. 4B

RETRIEVABLE STENT AND METHOD OF USE THEREOF

This application claims benefit of Provisional No. 60/295,128, filed Jun. 1, 2001.

FIELD OF THE INVENTION

The present invention relates generally to a removable stent and an assembly for its delivery or removal from a target site. The present invention particularly relates to a removable stent and system for its use in a medical procedure involving blood vessels, ducts, treatment of enlarged prostate gland, coronary artery disease and the like.

BACKGROUND OF THE INVENTION

Stents are used in a wide variety of medical procedures where the permanent expansion of an occluded vessel is desired. Usually, stents are constructed of a metal cylinder that is implanted into a patient at the site of obstruction. In a patient suffering from an occluded vessel, balloon catheterization or balloon angioplasty is often the prescribed treatment. However, following such a procedure, restenosis or re-narrowing of the occluded tissue often occurs. Therefore, stents were developed and are used to optimize and improve the initial and long-term outcome in patients treated for an obstructed vessel. In addition to obstructions, stents are also used to provide support for a graft during healing of reconnected vessels. Diseases most often treated using a stent include coronary artery disease, benign prostatic hyperplasia (also referred to as an enlarged prostate gland), and other medical indications where expansion of a lumen, vessel or duct is desired. As such, a variety of stent systems have been developed for medical use. See, for example, U.S. Pat. Nos. 5,100,429; 4,762,128; and 4,800,882.

Although the development of stents for use in medical procedures has been a major advance in treating a narrowed lumen, a variety of complications can and do occur in connection with either the delivery of the stent or, at a later time, following deployment of the stent in vivo. Such problems or complications include failure of proper deployment of the stent, misalignment, dislodgement, or damage of the stent after it is deployed, or re-occlusion of the vessel over time once the stent is inserted. In these cases, removal of the stent is desired. Devices and/or assemblies allowing for the extraction of a stent are known and include, for example, U.S. Pat. Nos. 5,474,563; 5,624,450 and 5,411,507. In particular, Hendrik, U.S. Pat. No. 5,624,450 describes an assembly for the removal of an implanted stent. The assembly entails use of an expandable element having an adhesive outer surface. The expandable element is connected to a pulling device. Insertion followed by expansion of the expandable element inside the faulty stent causes its attachment (adhesion) to the inner surface of the stent allowing the user to then "pull" the stent out. A particular disadvantage in this system is that it is unreliable, as attachment of the expandable element to the stent occurs by adhesion. As a result, a more reliable and effective removal system is desired.

An example of an additional stent removal system may also be found in U.S. Pat. No. 5,474,563, which describes a system for removal of a cardiovascular stent device from a blood vessel. The system includes a self-expanding elastomeric stent and an extraction catheter for removal of the cardiovascular stent. The extraction catheter is especially designed so as to specifically engage with projections located on the stent. Removal of the stent occurs by engaging the extraction catheter with the projections. One disadvantage of this extraction system and other similar systems is the requirement for complex extraction instrumentation as well as specific and intricate maneuvering by the physician to engage the extraction tool with the stent.

The above-described removal systems (and other similar devices not specifically described) offer advantages, including effectiveness and safety to both the user and the patient. However, it has been discovered that an obstacle or disadvantage to such devices is that their use is complicated. Additionally, even with the more simple removal systems, the susceptibility of separation of the removal device from the stent during use result in major limitations to the reliability of these systems.

In view of the above, it is apparent that there is a need to provide a removable stent and a system which allows for reliable and minimally traumatic removal of a stent from an in vivo target site. There is also a need to provide a removable stent and system that is efficient, simpler to use for the physician and easy to maneuver in vivo. A reliable and efficient removal system would reduce the overall procedure time required, reduce possible trauma to the lumen wall during use, and therefore reduce patient discomfort during recovery. Such removal systems include properties that reduce the amount of effort required by the physician prior to and during use of the system as well as properties that ensure the system remain intact during removal of the stent.

OBJECTS AND SUMMARY OF THE INVENTION

In view of the foregoing, it is an object of the present invention to provide a removable stent device that addresses the limitations and disadvantages associated with prior removal devices, yet meets the needs of the users.

A further object of the invention is to provide a removable stent system that is efficient, requires minimal effort by the user and that is reliable.

Still another object of the invention is to provide a removable stent assembly having a collapsing element configured around the circumference of the stent so as to allow retrieval of the stent by collapsing one end of the stent to a smaller diameter.

A further object of the invention is to provide a stent removal system where removal of the stent can be achieved by use of a simple removal tool having a grasper attachment. In one aspect of the invention, a stent removal system for removing a stent from a target site in a patient is disclosed. The system can include a removable stent that is collapsible at a proximal end by engagement of a collapsing element with a removal tool. The collapsing element can be a lasso or a discontinuous lasso configured so as to collapse the proximal end of the removable stent for removal from a body site. Alternatively, the collapsing element can be a hook that is movable between an up and a down position. The removal tool is configured so as to allow coupling to the collapsing element of the removable stent. The removal tool can be configured as a tube having a slot at one end allowing for its coupling to the collapsing element. The stent removal system can also include a grasper element designed to aid in the removal of the stent by attachment to a removal tool or a delivery tool.

An additional object of the invention is to provide a method of removing a stent in vivo using a stent removal system.

These and other objects not specifically enumerated herein are believed to be addressed by the present invention which contemplates a stent removal system for removing a stent from a body site that includes a removable stent having a collapsible proximal end, a collapsing element and a removal tool.

BRIEF DESCRIPTION OF THE DRAWINGS

FIG. 1 is a side view of a preferred embodiment of the present invention in situ including a removable stent having a collapsible proximal end, an inner lumen and a collapsing element;

FIGS. 2A and 2B are enlarged views of the area of a removable stent having a hinged hook collapsing element depicting the hinged hook in upright (FIG. 2A) and down (FIG. 2B) positions;

FIG. 3 is a cross-sectional view of a removable stent along the 3—3 line of FIG. 1;

FIGS. 4A and 4B are cross-sectional views through the hinge region of a hook type of collapsing element;

DETAILED DESCRIPTION OF THE INVENTION

Figure 6:
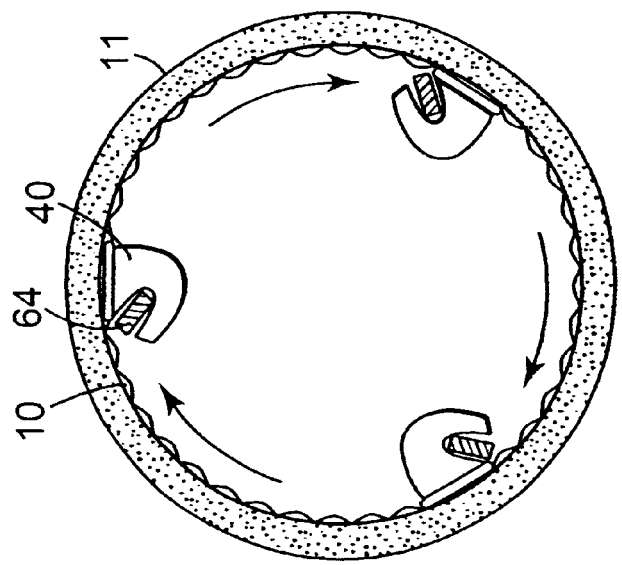
FIG. 6 is a cross-sectional view of a removable stent along line 6—6 of FIG. 5.

FIG. 1 shows a representative view of a removable stent 10 in situ within a body vessel 11. For convenience and ease of comprehension, the medical device referenced in the text and figures of the present disclosure is a stent. However, it should be noted that other medical devices or prosthesis including, but not limited to, balloons, stent coverings, vascular grafts, or other implantable devices, are also within the scope of the claimed invention.

The removable stent 10 is an intraluminal prosthesis or device having proximal 22 and distal ends 24 that are open. The removable stent is generally tubular in shape and has an outer surface 30 which contains an inner lumen 32 that extends axially between collapsible proximal 22 and distal ends 24. A removable stent includes collapsing elements 40, which aid in collapsing or compressing the stent 10 for its removal from an intralumenal site. The collapsing element 40 of the stent is a feature that aids in its efficient and easy removal from a body lumen. As used herein, the term "proximal" is intended to refer to the end of the stent closest to the physician when deployed at a target site, or the end that will be collapsed for removal of the deployed stent from its target site. The "distal" end is intended to refer to that end which is opposite to the proximal end 22.

A removable stent 10 can be of the type that is self expanding, or of the type that is expandable using a balloon mechanism. Methods for the construction, manufacture or deployment of self-expanding stents are known in the art and are described, for example, in U.S. Pat. No. 5,356,423 as well as in U.S. Pat. No. 4,655,771. Balloon expandable stents are also known in the art and are described, for example, in U.S. Pat. No. 4,893,623. Alternatively, the stent can be expandable by any other means, or can be of any variety of expandable prostheses or intralumenal implantation devices that include an element capable of collapsing or constricting the stent from an end, such as the proximal end.

Referring to FIG. 1, a removable stent 10 can be constructed so as to have a mesh structure 26. The mesh can be made of elongate elements, such as metal wires, that are woven, braided, or stamped. Alternatively, the mesh-work can be formed from any other type of material or structure so long as it is biocompatible and of sufficient rigidity so as to support patency of a body lumen or target site when implanted in vivo. Biocompatible materials suitable for such construction include, for example, stainless steel, alloys, composite materials, or plastics. The removable stent can also be constructed of a flexible or non-metallic material such as an elastic polymer or rubber, medical-grade nylon or polyester, or any material that is either itself collapsible or can be formed or configured to be compressible.

Figure 7:
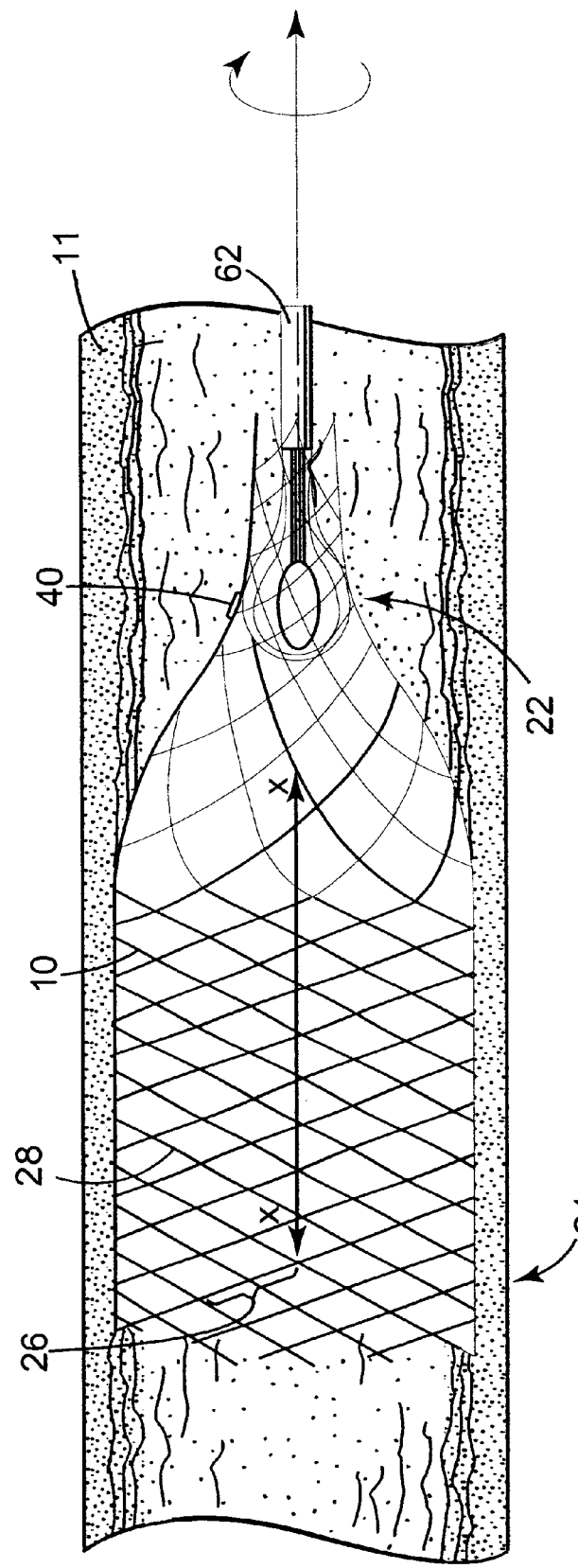
FIG. 7 is a side view of a removable stent in situ with the proximal end in the collapsed position.

In a preferred embodiment, as shown in FIGS. 1 and 7, the removable stent 10 is a braided tubular mesh 26, constructed of a collection of wires 28 (approximately 24 in number) held together by friction. The wires are formed or woven in such a way so as to facilitate and maintain radial expansion of the stent when deployed in vivo (See FIG. 1), while also allowing for radial compression of the stent when pulled along its longitudinal axis (FIG. 7). The expansion/compression feature of the removable stent 10 is designed such that application of a pulling force along the stent's longitudinal (x-x) axis results in radial compression and reduced lumen diameter. Release of the longitudinal force returns the stent to its deployed radially expanded dimension. This feature of the removable stent is similar to the mechanism employed in a child's Chinese handcuff toy.

A collapsing element 40 can be of a variety of structural configurations. The collapsing element 40 is preferably located at or near the proximal end 22 of the removable stent 10 as this is generally the end from which the physician will first encounter the stent during a removal procedure. In a preferred embodiment, a removable stent can include a collapsing element 40 designed as a clasping structure that is located within the inner lumen 32 of the removable stent as shown in FIG. 1 and 3. FIG. 3 is a cross-sectional view of a removable stent taken along the 3—3 line at the proximal end 22 of the removable stent 10 of FIG. 1. Such a collapsing element 40 (also referred to herein as a "hinged hook" or a "hook"e) is movable between a first and a second position. Therefore, as illustrated in FIG. 2 the hook elements 42 can be lifted into an upright or "up" position (FIG. 2A) for engagement with and extraction by a removal tool, or can be pushed into a "down" position (FIG. 2B) where it lays flat against the inner wire surface 42 of the removable stent when the stent is deployed in vivo. As illustrated in FIG. 3, when in the "up" position, the hooks 40 protrude away from the inner surface 30 of the stent into the inner lumen 32. A removable stent having a hinged hook type of collapsing element 40 will preferably include 2 to 3, or 3 to 4 hooks, spaced equally along the inner circumference or surface 30 of the removable stent.

FIGS. 2A and 2B are enlarged views illustrating a hook type of collapsing element 40 of a removable stent when deployed in vivo. When in the first or "down" position (FIG. 2B), the hook element 40 resides substantially parallel to or flat against the inner surface of a cross wire 42 of a stent. The ability of the hook 40 to lay flat against the inner surface of the removable stent ("down" position) is particularly advantageous in that such a collapsing element 40 will not interfere with the patency, impede the flow, or increase the possibility of clot formation of a fluid through the stent. This is of particular concern when a stent is deployed in a blood vessel. A collapsing element 40 that is movable between an up and a down position allows for placement of the collapsing element 40 into a more accessible position for engagement with a removal tool. This aspect of the present invention provides a more versatile and effective removable stent.

A hinged hook type of collapsing element 40 includes an upper region that is curved or shaped as a hook 44. The lower or bottom portion 46 of the collapsing element 40 is configured so as to enclose or wrap around a wire 43 of the stent so as to function as a hinge. The collapsing element 40 can be attached to a stent wire 43 at the inner surface of the removable stent. A hinged hook 44 can be designed or configured so as to snap onto a stent wire 43 with a portion 46 of the hinged hook disposed toward the outer surface of the stent. Once snapped into place, the hinged hook 44 can be pushed or slid along the stent wire 43, passing underneath a crossing wire 41, so as to position the hook 44 underneath a cross wire 42 as shown in FIG. 2B.

In addition, a hook type of collapsing element can be configured so as to include tab components, which allow it to be easily snapped or clipped onto a stent wire. Referring to FIGS. 4A and 4B detailed cross-sectional views through the hinge portion 46 of a hook 44 illustrate two exemplary designs of tab components of a hook hinge region. In the first design (FIG. 4A), the tab gap element 8 is an extension of the hinge portion 46 that, when pressed, will become captured in the hinge latch 47 which is an extension of the hook 44. In the second design (FIG. 4B), the hinge latch 47 is pressed such that it becomes captured by the tab gap element 8. Both of these hinge designs allow rotational movement of the cross wire 43 relative to the hook 44. That is, the hinge 46 portion of a hook type 44 of collapsing element 40 allows the collapsing element to be movable between its deployed, "down" position and a removable "up" position. A hinged hook 44 type of collapsing element as described herein is also advantageous in that the tab gap design reduces undesired movement of the hook element 44 between its two positions (upright or down) by virtue of how the tab gap design is comprised around and in frictional contact with the cross wire 43. Therefore, a hinged hook is preferably manufactured of a material that maintains a certain degree of resistance so as to ensure the collapsing element remains in either the up or the down position, as is desired by the physician during use. A hinge material can be manufactured of a same material as the stent wire, such as stainless steel or plastic. An optimal method of fabricating and handling a hinged hook is by continuous metal stamping on a band or a ribbon.

Figure 5:
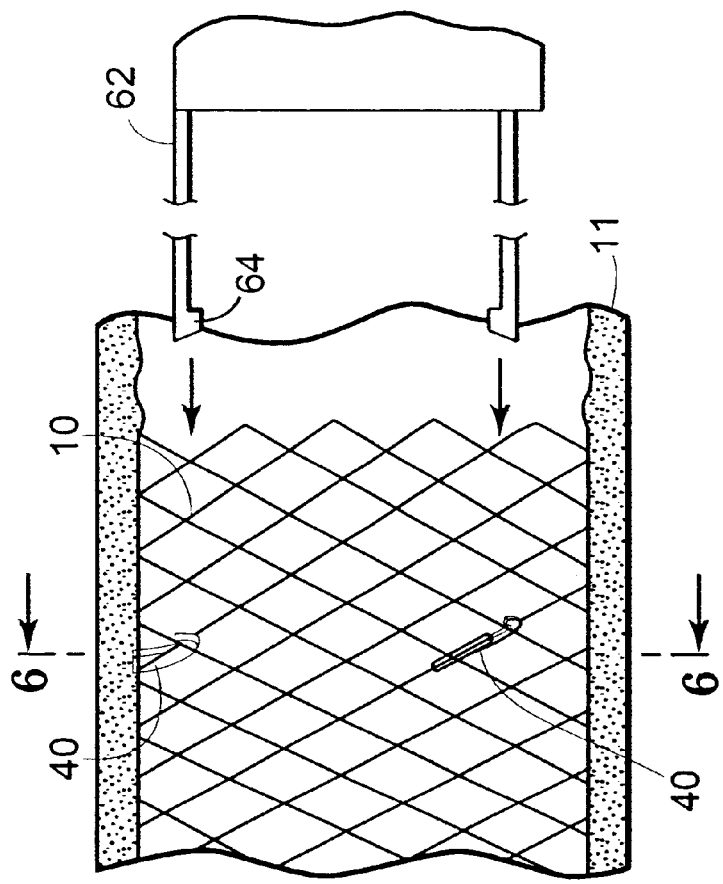
FIG. 5 is a side view of a removable stent including a removal tool for grasping a collapsing element of a removable stent.

A stent of the present invention can be removed from an intralumenal site by collapsing one of its ends, such as the proximal end, with the aid of a removal tool. Several types of removal tools 62 can be used to remove a stent 10 of the present invention, as will be apparent to one skilled in the art. Referring to FIG. 5, a removal tool 62 suitable for use with a hook type of collapsing element 40 can be designed to have coupling structure 64 for engaging the hook elements 40. The stent 10 can then be collapsed beginning at its proximal end 22 using the removal tool 62 to grasp the hooks 40 and to apply a pulling force. FIG. 6 illustrates a cross-sectional view of a removable stent having hook elements 40 engaged with a removal tool. As indicated in FIG. 6, application of a rotational force on the constricting elements 40 via the coupling means 64 collapses the stent 10 radially inward.

In a preferred embodiment, a removal tool 62 can take the form of a standard stone basket tool. One such tool includes a stone basket as manufactured by Cook Urologic. In this embodiment, the strands forming the basket of the tool engage the hooks 40 as shown in FIG. 6.

FIG. 7 illustrates a stent 10 of the present invention during removal from an intralumenal site 11. Radial constriction begins at the proximal end 22 of the stent 10 extending toward the distal end 24 longitudinally, as the stent 10 is pulled by a removal tool 62 coupled to the collapsing elements 40. Radial compression and collapse of the stent 10 beginning with the proximal end 22 allows the physician to easily withdraw or ensnare the stent 10 into an endoscope sheath for its removal from an in vivo intralumenal site 11. This aspect of the removable stent 10 is particularly advantageous to achieving the goals of the invention in that a stent 10 having a collapsible end allows for easy manipulation of the stent 10 into a catheter or endoscope sheath to completely remove the stent 10 from the patient's body.

Figure 8:
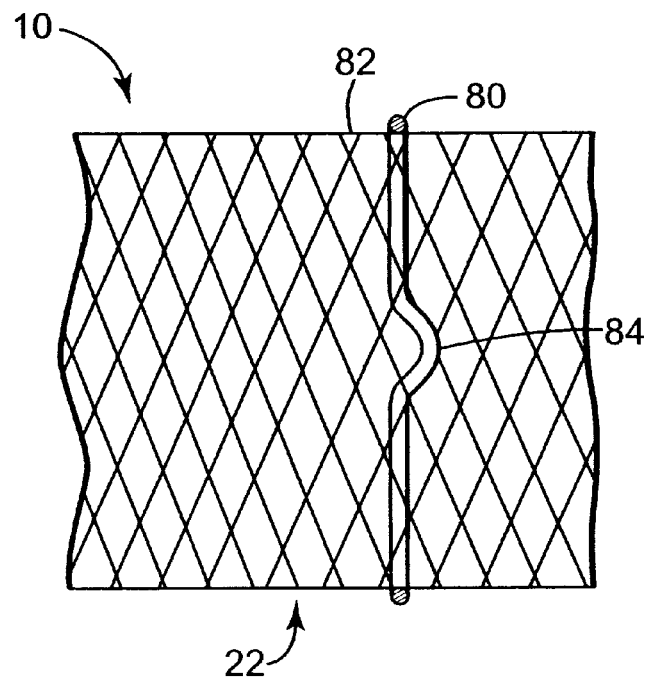
FIG. 8 is a view of a removable stent having a lasso collapsing element.

Referring to FIG. 8, a collapsing element can also be configured as a lasso 80 situated around the circumference of the proximal end 22 of a stent 10. The lasso 80 is constructed of a wire which functions as a noose capable of constricting or tightening itself around the outside surface 82 of the stent 10. The lasso 80 can include a loop region 84, which allows for engagement of a removal tool 101 to grasp and remove the stent 10 (see FIG. 10). The loop region 84 of the lasso 80 is disposed internally within the stent 10 with the remainder of the lasso wire 86 wrapped externally around the stent 10. Alternatively, the lasso 80 can be woven into and out of the stent surface 82. Therefore, the lasso 80 is preferably incorporated substantially around the circumference on the outside surface 30 of the stent 10.

Figure 9:
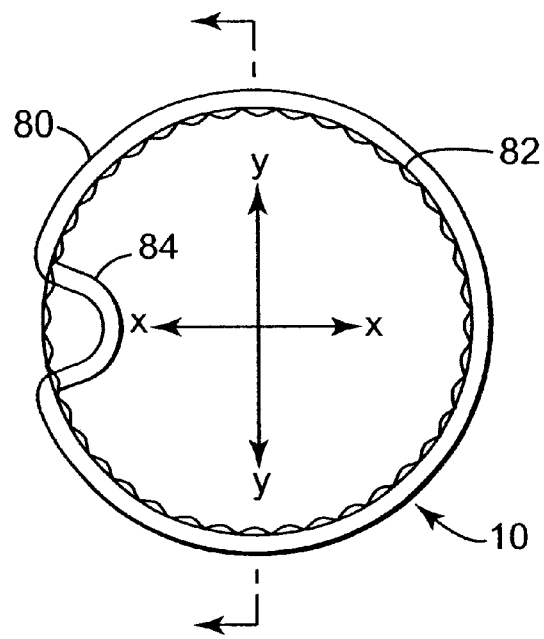
FIG. 9 is a cross sectional view through the proximal end of a removable stent having a lasso collapsing element.

As illustrated again in FIG. 9, the inner lumen 90 of the removable stent 10 has a cross-sectional diameter, along its x-x, or its y-y axis, which dimensions can vary depending on use. FIG. 9 shows a cross-sectional view of a removable stent 10 when expanded. The diameter of the inner lumen 90 can vary between a relatively larger diameter such as when the stent is deployed, and a significantly smaller diameter. Therefore, when the proximal end 22 of the stent is collapsed, through constriction of the lasso 80, the inner lumen will have a reduced cross-sectional diameter allowing for its extraction from an intralumenal site (see FIG. 11). This aids the physician in removing the stent from its target site with minimal damage or trauma to the surrounding tissue.

Figure 10:
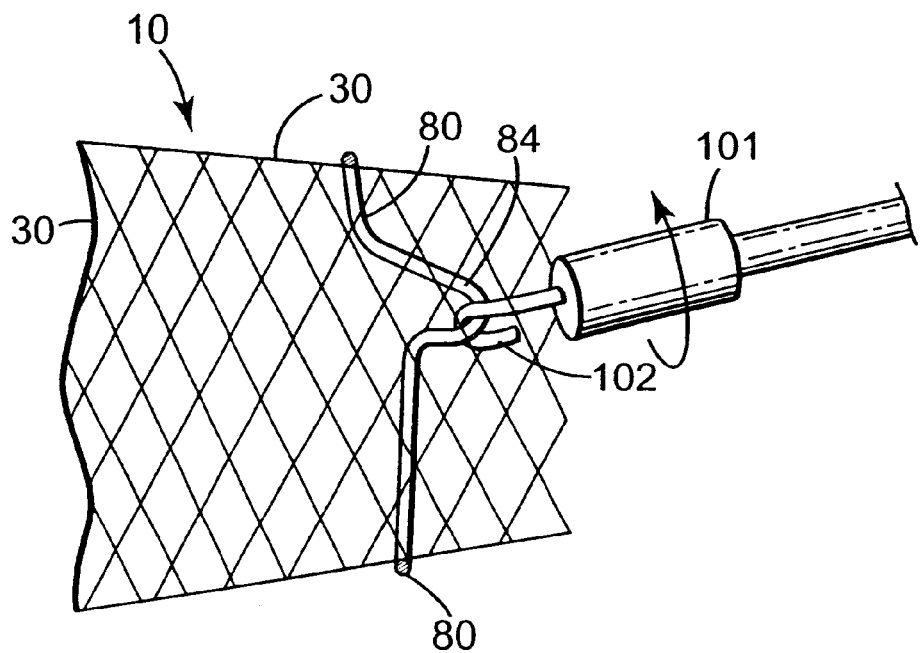
FIG. 10 is a view of a removal tool and a removable stent having a lasso collapsing element.
Figure 11:
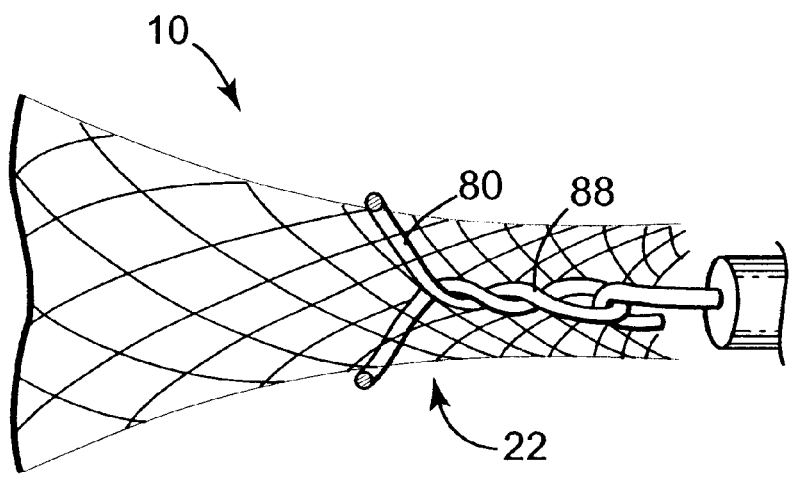
FIG. 11 is a view of a removal tool grasping a removable stent.

FIGS. 10 & 11 shows views from internal perspectives (inside viewing outward) of a removable stent 10 during collapse and removal of the stent 10. The lasso 80 type of collapsing element functions by radial contraction, which collapses a removable stent 10 from an expanded diameter (FIG. 10) to a reduced diameter (FIG. 11). The loop region 84 of the lasso 80 protrudes into the inner lumen of the removable stent 10, thereby allowing the physician to grasp the lasso 80 by a hook element 102 disposed at the end of the removal tool 101 (FIG. 10). Constriction of the proximal end 22 of the stent 10 is achieved by rotating the removal tool 101, which causes the lasso to twist upon itself, thus also collapsing the stent 10. Alternatively, the lasso can be designed to include internal elements such as a ball, a hook, or a loop that assists in locating as well as operating the lasso. The lasso 80, therefore, constricts or collapses the proximal end 22 of the removable stent 10 by radial tightening 88 of the lasso 80 upon itself. A lasso type of collapsing element can be constructed from permanent materials (stainless steel, or metal wire, for example) or from temporary degradable materials.

Figure 12:
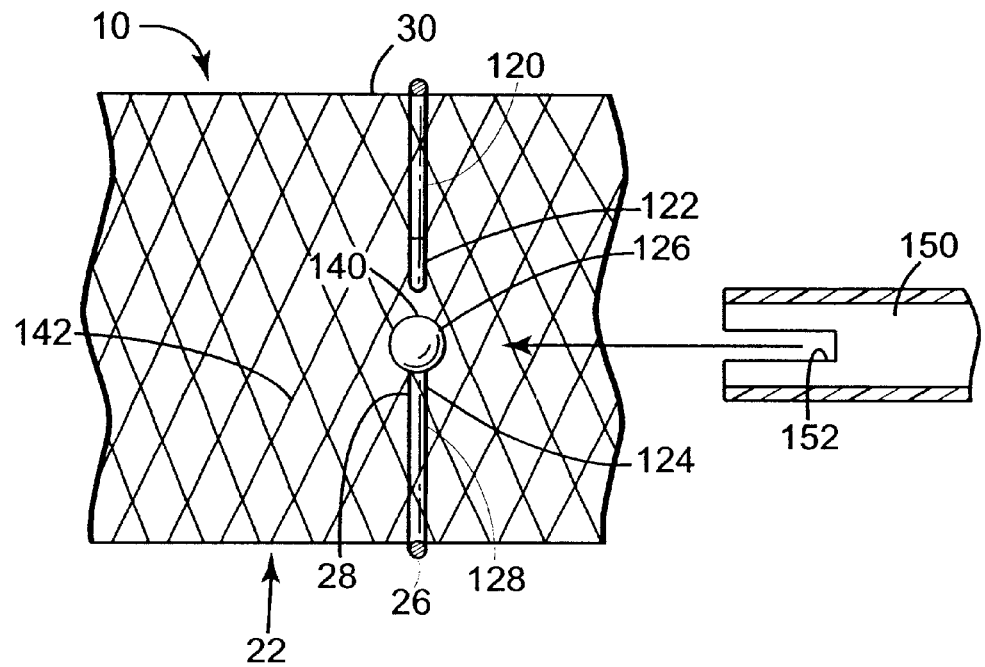
FIG. 12 is a view of a removable stent having a discontinuous lasso collapsing element.
Figure 13:
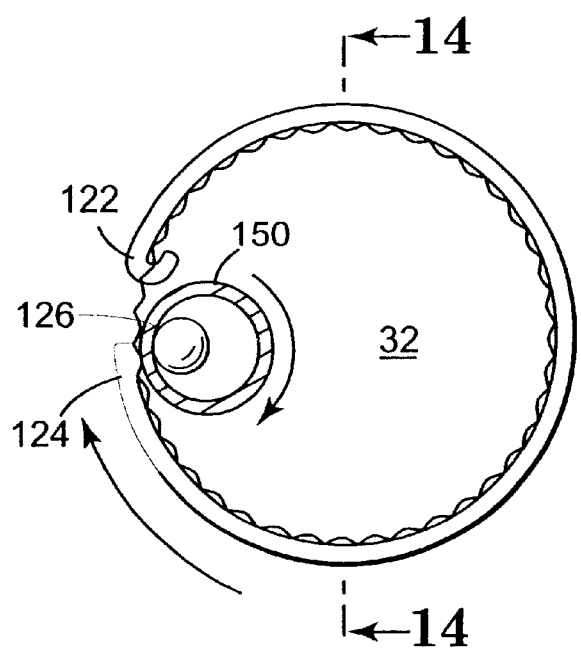
FIG. 13 is a cross sectional view through the proximal end of a removable stent having a discontinuous lasso collapsing element.

Referring to FIGS. 12–15, in a further embodiment of the present invention, the collapsing element of a removable stent 10 need not extend over the entire circumference of the removable stent 10 as a lasso or a noose, but can be a collapsing element that is a discontinuous type of lasso. Referring to FIG. 12, the collapsing element includes a discontinuous lasso 120 having a first end 122 and a second end 124. The first end 122 is attached or anchored to the proximal end 22 of the removable stent 10. This attachment can be permanent if desired. The second end 124 of the collapsing element or discontinuous lasso 120 is not attached to the stent, but is freely associated with the stent 10. This allows for the free expansion of the stent as needed in vivo. At least a portion of the discontinuous lasso between its first and second ends is juxtaposed, adjacent or interwoven to the outer surface 30 of the stent 10.

A discontinuous lasso 120 can be a wire 128 that is woven in between the wires 26, 28 forming the removable stent 10. The discontinuous lasso 120 is connected to the removable stent 10 at a diamond 140 that is formed by the weaving of the wires 142 comprising the removable stent 10. The second end 124 of the discontinuous lasso 120 includes a ball 126 which protrudes into the lumen 32 of the stent 10, thereby allowing the user access to the discontinuous lasso 120 by insertion of a removal tool 150 into the lumen of the stent 10. The diameter of the ball 124 is slightly larger than the diagonal diameter of the diamond 140, thereby maintaining the ball 126 within the inner lumen 32 of the stent 10. When the removable stent 10 is expanded, the ball 126 is seated partly within a diamond 140. The removable stent 10 can, therefore, freely expand to any given cross-sectional diameter without being restricted by its collapsing element. The design of a discontinuous lasso type of constricting element allows for a freely associated second end 124 which does not restrict expansion of the removable stent 10.

Figure 14:
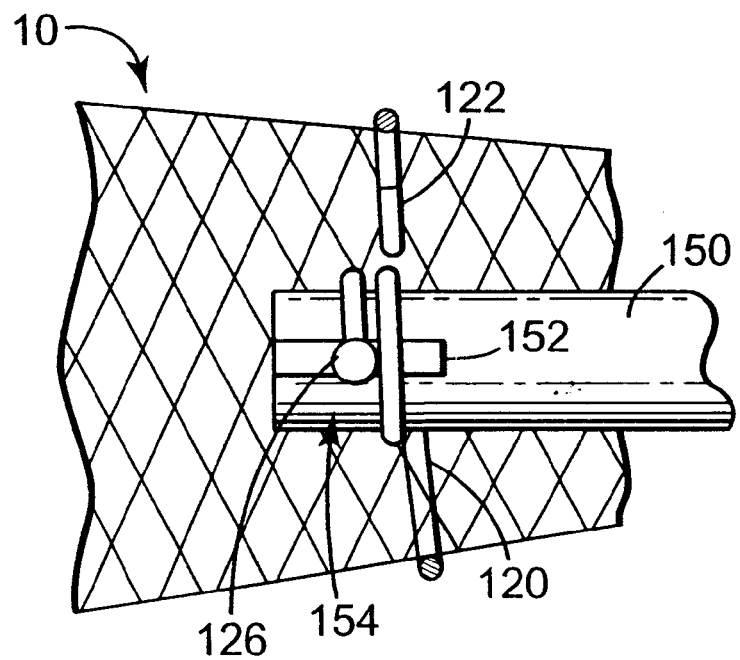
FIG. 14 is a view of a removal tool grasping a removable stent.
Figure 15:
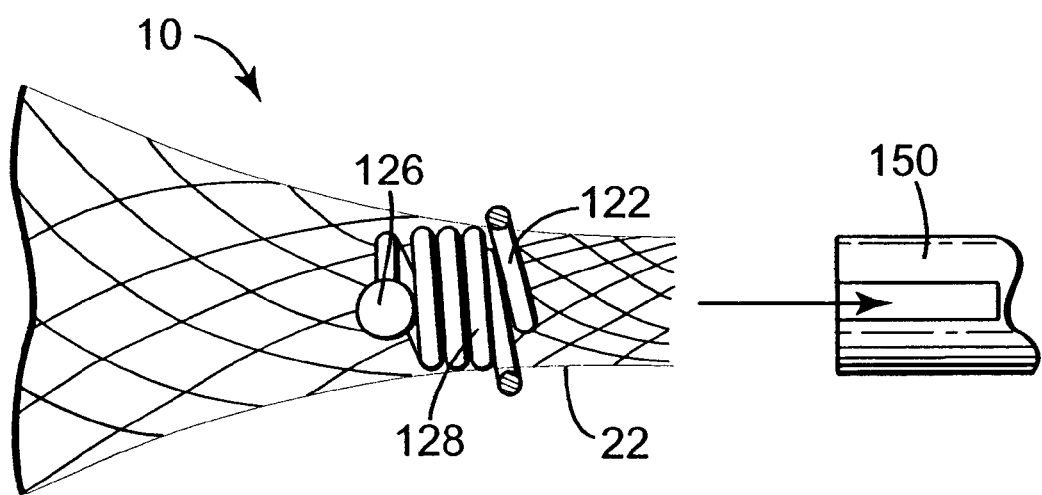
FIG. 15 a view of a removal tool grasping a removable stent.

Referring to FIG. 14 & 15, in order to collapse and remove a stent having a discontinuous lasso type of collapsing element 120, a removal tool 150 is used. An example of such a tool is shown in FIG. 14. The removal tool 150 can be configured as a cylindrically shaped tube having a slot 152 disposed at its end. The removal tool should be sufficiently rigid so as to allow the user to easily maneuver and engage the ball 126 of the collapsing element 122 into the slot 152. The slot 152 is slid underneath the ball 126 of the collapsing element 120 (FIG. 14), thereby lifting the ball 126 out of its seating within the stent 10. Once the ball 126 is lifted, the removal tool 150 is twisted, wrapping the wire of the discontinuous lasso 128 around the outer surface of the removal tool 150. Because the pulling force of the discontinuous lasso 120 and the holding force of the removable stent 10 are at the tip 154 of the removal tool 150 (FIG. 14) the proximal end 22 of the stent 10 is easily collapsed (FIG. 15), enabling the physician to pull or withdraw the collapsed stent away from the implanted site in vivo.

In another embodiment of the invention, shown in FIGS. 16 to 21, the removable stent 10 includes one or more eyelets or loops 170 formed at or near the ends of the elongate elements or wires 172 of the stent 10. The loops 170 can be shaped either before or after the wires 172 are assembled into the mesh-structure that forms the stent 10. The shape of the loops 170 can include "p"-shaped, helical, twisted, oval, circular, diamond, square or any other similar configuration that forms a hole capable of receiving and/or capturing a cord-like member, such as a lasso 80. The design and alignment of the loops 170 at the ends of the wire elements 172 are configured to prevent the loops 170 and/or lasso 80 from projecting or extending into the interior of the stent 10. This, in turn, reduces the potential for encrustation or clot formation within the lumen of the implanted stent 10.

In one embodiment, at least one end of the wire element 172 is twisted or wound into a loop 170. Although the material characteristics of the wire element 172 maintain the end of the wire element 172 in a loop configuration, a resistance laser weld, crimp or other connection can be made at the location on the loop 170 where the wire element 172 crosses over itself. The resistance weld can be used to further secure the end of the wire element 172 in a permanent loop arrangement.

Figure 17:
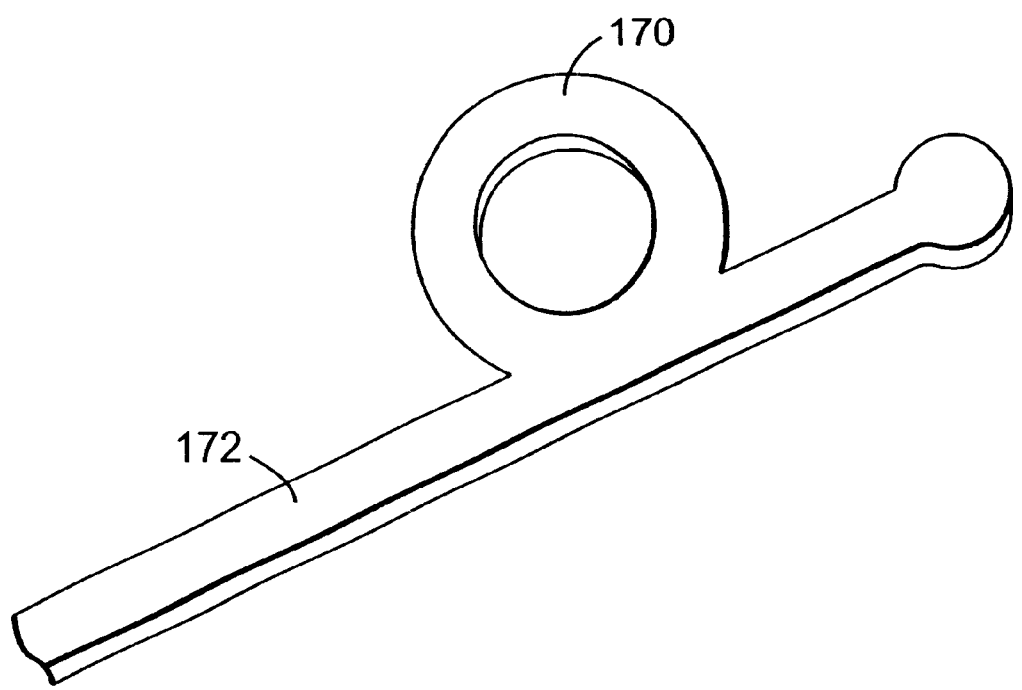
FIG. 17 is a detailed view of an alternate embodiment of the loop of FIG. 16.

In an alternate embodiment, the elongate element 172 can be laser-cut, stamped or punched from a sheet of material. As shown in FIG. 17, at least one loop 170 is formed at an end of the stamped element 172. Other embodiments of forming the loop 170, though not specifically described herein, are also included within the scope of the claimed invention.

Figure 16:
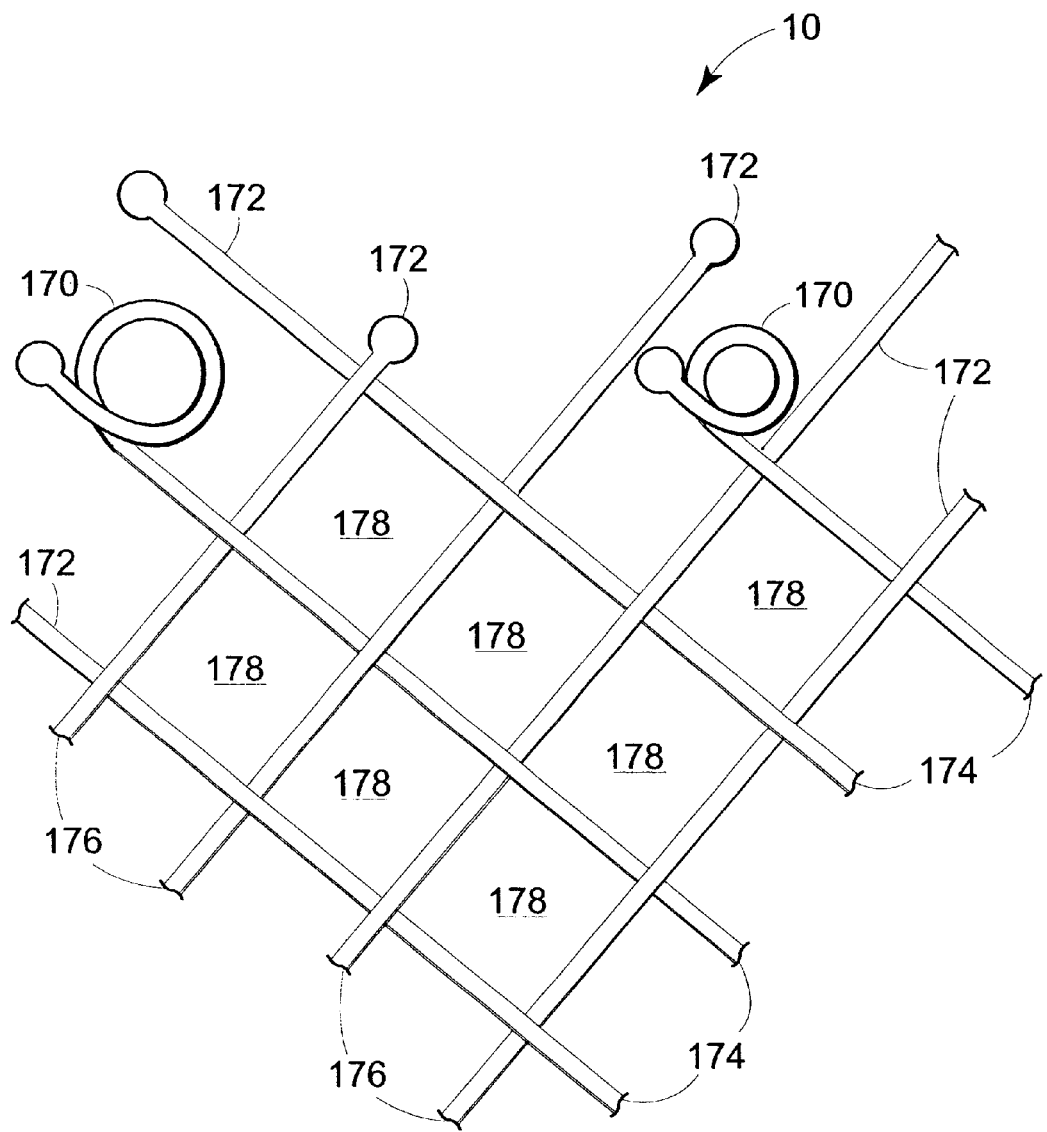
FIG. 16 is an enlarged view of an area of an alternate embodiment of a removable stent having eyelets or loops formed near the end of the stent.

Referring to FIG. 16, the mesh-structure of the stent 10 is formed from two sets or groups of parallel wires 172. The first set of parallel wires 174 is placed at approximately a 90 degree angle with respect to the second set of parallel wires 176, forming a diamond-shaped pattern 178 of wire elements 172. However, the actual placement of the two sets of parallel wires 174, 176 may vary within the range of 10 degrees to 170 degrees. As shown in FIG. 16, a loop 170 is formed at or near an end of every other wire 172 of the first set of parallel wires 174. The configuration of the first set of wires 174, in particular the placement of the wires 172 so that each wire end rests on the external surface of a wire element 172 (whereby the external surface of the wire element 172 corresponds to the outside surface 82 of the stent 10, not shown) from the second set of wires 176, further enhances the constriction characteristics of the stent 10. In addition, this configuration also prevents potential flaring of the distal end of the stent 10 as the proximal end 22 of the stent 10 is constricted or collapsed during stent removal. Flaring of the distal end of the stent 10 not only impedes stent removal, but also causes the wire ends to anchor or embed into the wall tissue of the lumen. Thus, the loop design at the ends of the wire elements 172 also mitigates potential tissue trauma associated with the stent removal procedure.

Figure 18:
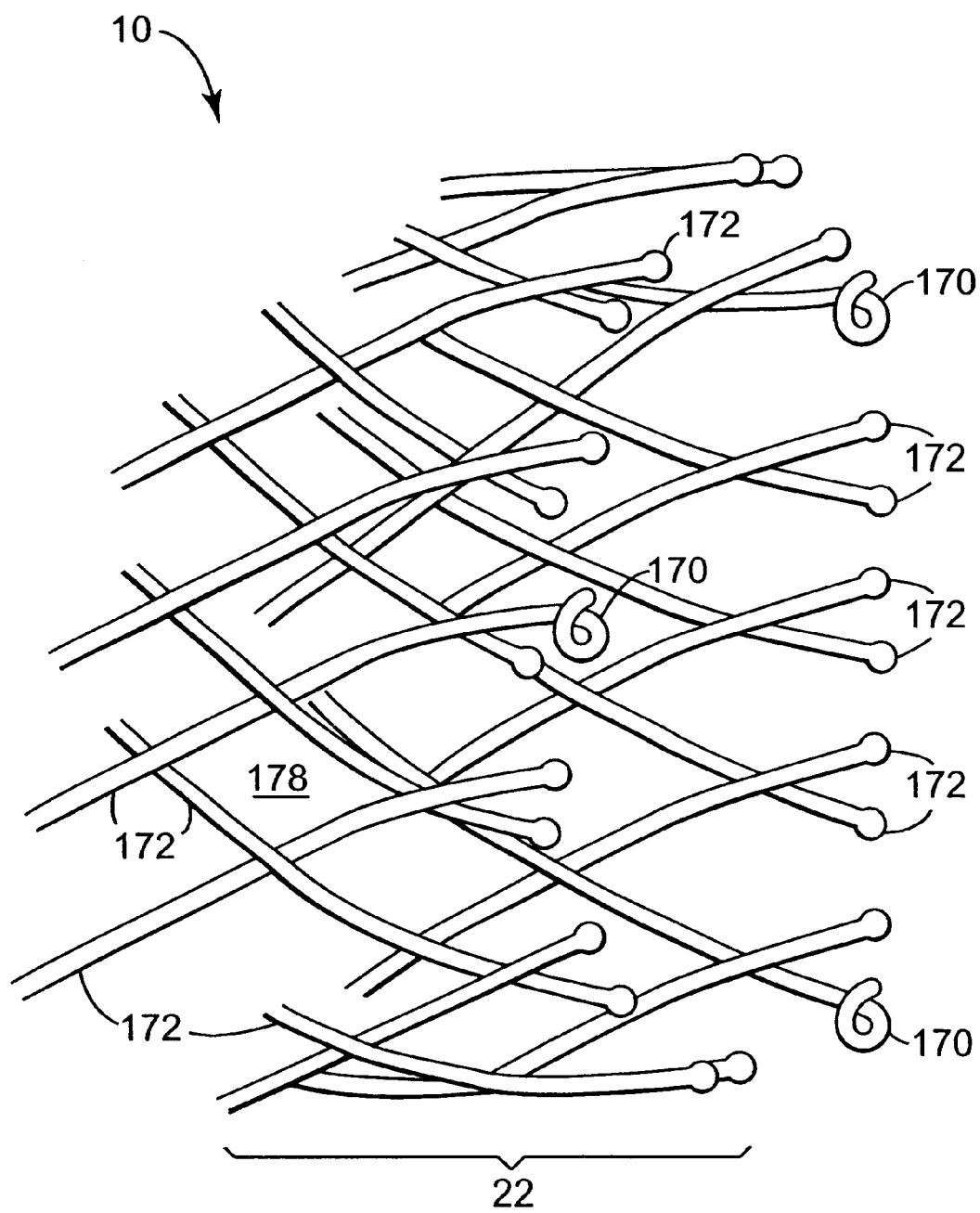
FIG. 18 is an enlarged view of an area of an alternate embodiment of the removable stent of FIG. 16.

In another embodiment of the invention, shown in FIG. 18, a total of at least three loops 170 are formed at the ends of the wires 172 near the proximal end 22 the stent 10. In general, the loops 170 are formed at the ends of the wires 172 and a lasso-type element is woven through the loops 170. Placement of the loops 170 at the ends of the wires 172 improves user accessibility to the lasso for facilitated stent 10 removal. In another embodiment, the loops 170 can be formed anywhere within the region approximately two diamonds 178 distal to or 10 mm or 5 mm (0.39 inches or 0.020 inches) from the ends of the wire elements 172.

Figure 19:
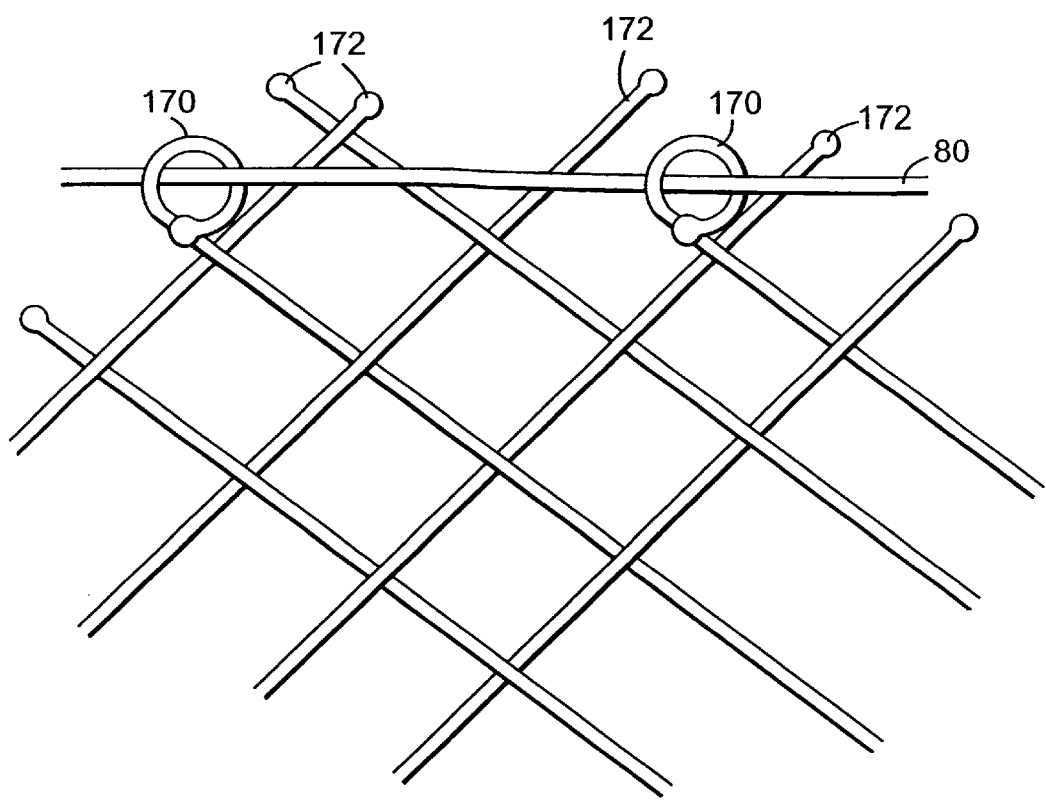
FIG. 19 is a partial view of the removable stent of FIG. 16 having a lasso-type collapsing element.
Figure 20:
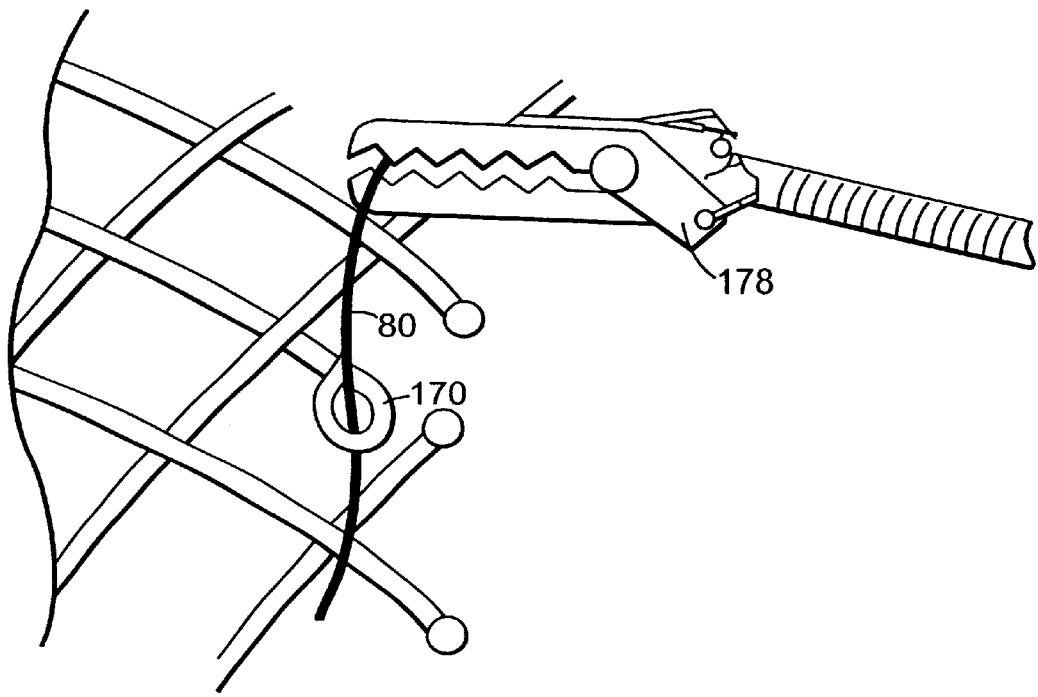
FIG. 20 is a partial side view of a removal tool and the removable stent of FIG. 17.
Figure 21:
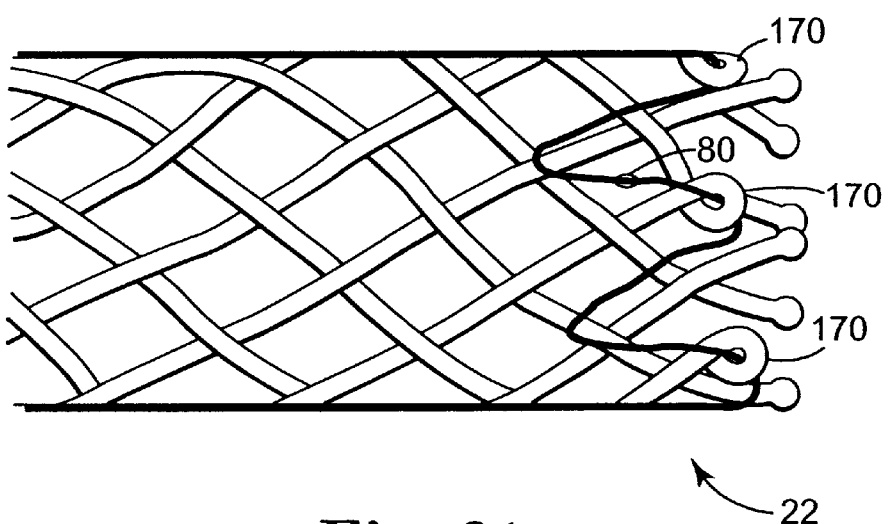
FIG. 21 is a side view of the removable stent of FIG. 17 in a constricted configuration.

As shown in FIGS. 19 and 20, the lasso 80 type collapsing element is woven or threaded through the loops 170 of the stent 10. In one embodiment, the lasso 80 type collapsing element is a flexible closed-loop or ring-like structure. When the stent 10 is in an expanded configuration, portions of the lasso 80 extending between each loop 170 are easily accessible for engagement from the end of the stent 10 in vivo using a standard alligator gripper or custom removal tool 178. As such, the stent 10 is removed from the lumen of the patient by twisting the removal tool 178 so that the lasso 80 wraps around the outer surface of the removal tool 178 or pulling the lasso axially. Because the pulling force of the lasso 80 and the holding force of the removable stent 10 are at the tip of the removal tool 178, the proximal end 22 of the stent 10 is easily collapsed, enabling the physician to pull or withdraw the collapsed stent 10 away from the implanted site in vivo. Referring to FIG. 21, during constriction of the proximal end 22 of the stent 10, the lasso 80 is configured so that it acquires a folded profile. The folded configuration of the lasso 80 prevents portions of the lasso 80 from hanging into the lumen and causing associated blockages or clot formations. As such, any slack or folds in the lasso 80 is generally held or captured between the external surface of the stent 10 and the tissue wall of the patient's lumen.

Figure 22:
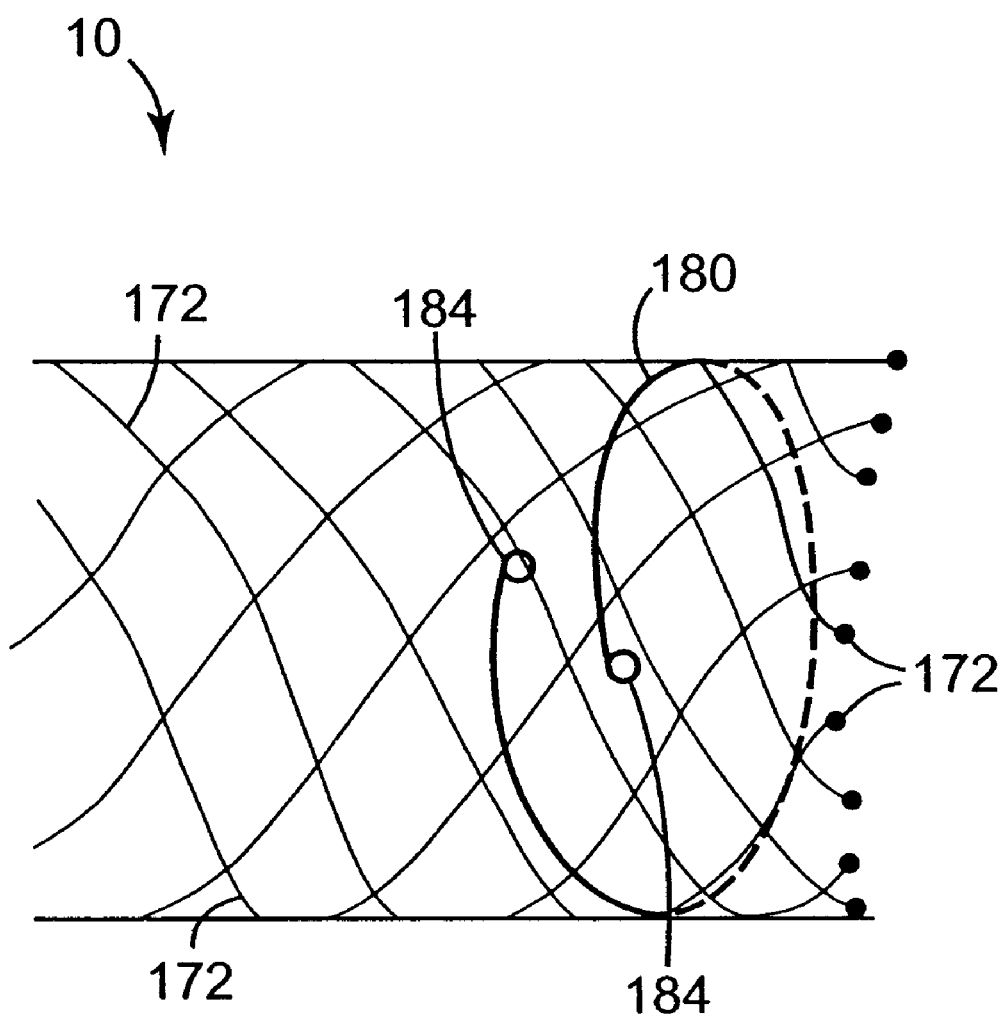
FIG. 22 is a side view of a removable stent and an alternate embodiment of a collapsing element.
Figure 23:
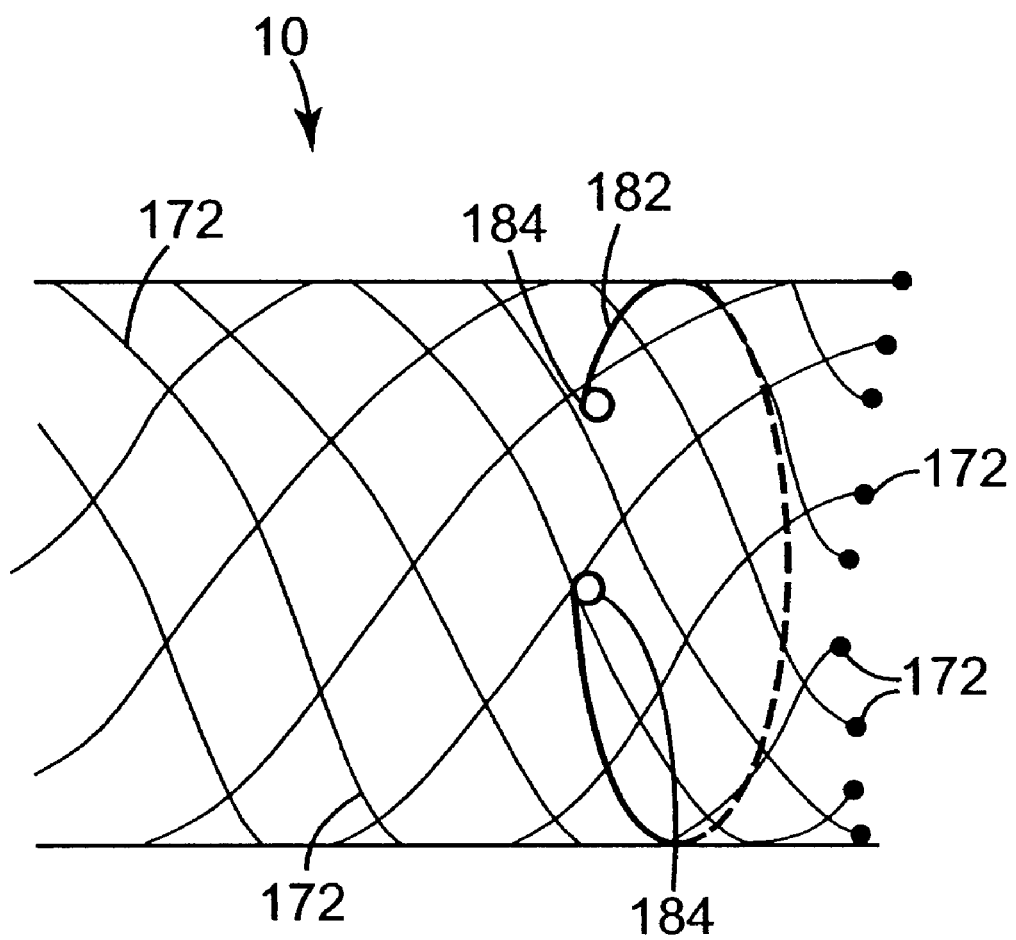
FIG. 23 is a side view of a removable stent and an alternate embodiment of a collapsing element.

In an alternate embodiment, the collapsing element of the removable stent 10 need not extend over the entire circumference of the removable stent 10 as a lasso or a noose does. As shown in FIGS. 22 and 23, the collapsing element can be a discontinuous spiral 180 or c-shaped 182 clip member. In general, the spiral 180 or c-shaped 182 clip member can be fabricated from a rigid or semi-rigid material. As with the elongate elements 172 of the stent 10, the clip member 180, 182 can be fabricated from a variety of materials including, but not limited to, laser cut, woven, braided, or stamped. Various other material types and configurations may also be used provided that the type of material or structure is biocompatible and of sufficient rigidity so as to support constriction of the stent 10. Examples of suitable biocompatible materials include, but are not limited to, stainless steel, alloys, composite materials, plastics, or other non-metallic materials such as an elastic polymer or rubber, medical-grade nylon or polyester.

In one embodiment, the spiral or c-shaped member 180, 182 is attached or clipped onto the external surface of the stent 10. To constrict the stent 10, a removal tool is maneuvered between the external surface of the stent 10 and the lumen of the patient and engages/grasps the ends 184 of the clip member 180, 182. Using the tool, the ends 184 of the clip member 180, 182 are then moved toward each other and/or, depending on the desired degree of constriction of the stent 10, past each other. Radial constriction of the clip member 180, 182 causes inward collapse or radial contraction the stent 10. In an alternate embodiment, one end of the clip member 180, 182 is attached or secured to the stent 10 (not shown). As such, the removal tool need only grasp or engage the unattached end of the clip member 180, 182, moving the free end of the clip member 180, 182 toward and/or past the secured end. As with the previous embodiment, constriction of the clip member produces radial contraction of the stent 10, without causing the stent 10 to rotate within the lumen of the patient.

Due to the dynamic nature of living tissue, ingrowth can occur around an implanted stent. As a result, it is sometimes necessary for the physician to resect or cut the implanted stent away from the surrounding tissue. As such, heated methods of resection are often used to cut the stent out. Therefore, a lasso type collapsing element 120 can be a wire constructed of a material that is resistant to heat during resection, such as a flexible carbon fiber substance. In addition, the discontinuous lasso 120 can be coated with an anti-adhesive substance such as heparin, or other pharmaceutical or chemical agent which aids in preventing adherence of tissue to the collapsing element.

As disclosed above, a collapsing element can be configured in a number of ways and is preferably designed so as to allow the user to grasp the stent and collapse the proximal end of the stent. It should be noted, however, that also included in the present invention is a removable stent having a collapsing element whose location is not at or restricted to the proximal end of the stent. For example, a collapsing element can be disposed anywhere along the length of the stent so long as the collapsing element is designed so as to be capable of collapsing an end of the stent. This allows for removal of the stent from an intraluminal site with minimal damage to adjacent tissue or intraluminal wall of the target site.

A variety of tools or devices can be used to grasp the collapsing element of a removable stent. In addition to the removal tool as described above, stone or basket extractors or grasping forceps known in the art can be used with the present invention. For example, with a removable stent having a hinged hook type of collapsing element, a physician can use a basket extractor to engage and grasp the hinged hooks. Using a stone extractor, for example, the physician will first position the hooks into their upright position (while viewing the deployed stent through a cystoscope). Once upright, the physician then engages the wires of the extractor with the hooks, thereby grasping the stent by the collapsing elements. By collapsing the wires of the extractor, the physician also pulls on the collapsing elements, thereby collapsing the proximal end of the stent. Once collapsed, the stent can then be pulled into the sheath of the cytoscope.

Figure 24:
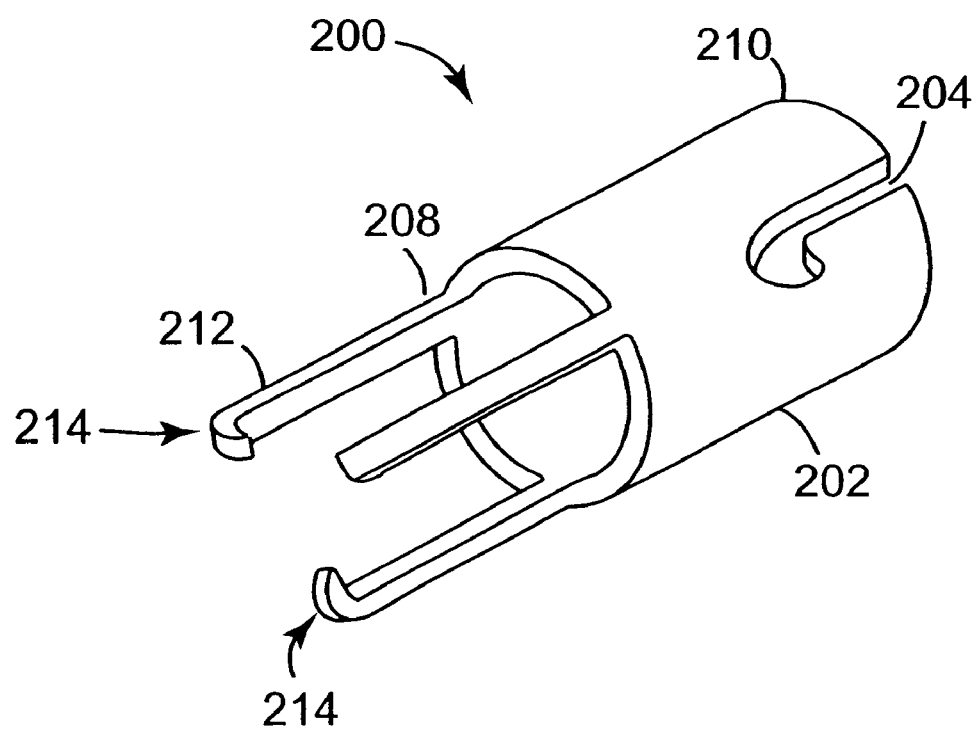
FIG. 24 is a view of a grasper device for attachment to a removal or a delivery tool.

An additional aspect of the present invention comprises a removal attachment or grasper for use with a delivery tool to engage or grasp the removable stent. FIG. 24 shows a view of a removal attachment 200 that can be used with a removal tool. Alternatively, such an attachment can be attached or used with a stent delivery tool. Removal tools suitable for use with a removal attachment include those described herein as well as others known in the art, such as the Urolume Delivery System. Stent delivery tools suitable for use with a removal attachment include the Urolume Delivery System.

The removal attachment includes a base portion 202 that is tubular in shape. The base portion 200 has a front end 208 and a back end 210. The base portion 202 includes an element 204 disposed at the back end 210 which locks the removal attachment 200 to a delivery tool such as a grapple. The front end 208 of the removal attachment 200 includes prong(s) 212 that are configured or shaped as curved finger-like projections that extend outward or away from the removal attachment 200. The prong(s) 212 can be manipulated so as to grasp or hook a collapsing element of a removable stent. One aspect of the removal attachment that is particularly advantageous to achieving the goals of the invention is that it is designed to be adaptable with a wide variety of tools used in the art for delivery and/or removal of a stent.

Method for Extraction of a removable Stent

The methods and devices of the present invention provide simple, accurate and stable removal of a stent or prosthesis from an intraluminal or other, site in vivo. The features of the invention, as described herein, provide a removable stent and system that is reliable and less awkward or cumbersome for the physician to use.

The present invention can be used for a variety of medical treatments where removal of a stent from a patient is or may be desirable. For example, in the treatment of an enlarged prostate gland, a stent is often placed in the patient's urethra, intraluminally at the site of compression by the enlarged prostate. The deployed stent is often intended as a permanent means of providing support and radial expansion to the constricted urethra so that urine flow from the bladder through the compressed site is remedied. However, failure of the implanted stent to function properly can occur. For example, over time, tissue ingrowth from the urethral wall through the openings of the stent wall can occur, resulting in reobstruction or restenosis of the lumen. The present invention is particularly advantageous in that it has elements allowing for its easy access, and removal in vivo should the need arise to remove or explant the stent after deployment. Therefore, the present invention can function as a permanently implanted stent or as a temporary or removable stent in vivo. Use of the present invention in medical indications requiring stent treatment adds a precautionary measure not provided in permanent stent implants or prostheses.

Depending upon the location of the deployed stent and/or the physician's preference, a removable stent can be extracted using a removal tool and withdrawn into a catheter or a sheath of a viewing instrument. For example, as shown in FIG. 10, with a removable stent 10 having a lasso type of collapsing element 80, a removal tool 101 having a hooked end 102 is first inserted into a patient's urethra through a viewing instrument, up to the site of the deployed stent. Once at the stent, the physician engages the hooked end of the removal tool 101 with the loop 84 portion of the collapsing element 80. The physician maneuvers by twisting or rotating the removal tool so as to cause the lasso 80 to constrict upon itself Tightening of the lasso 80 around the stent 10 collapses the proximal end 22 of the removable stent 10 (FIG. 11). The collapsed end of the removable stent is then easily aimed into the lumen of an extraction catheter or the sheath of a cystoscope. Once inside the lumen, the stent 10 is extracted by further pulling on the lasso 80, which is coupled to the stent. The remainder of the stent 10 is then pulled away from and out of its in vivo site.

Alternatively, as described previously, where a stent having an alternative collapsing element configuration is to be removed, there are a variety of commercially available devices that can be used as the removal tool. If the deployed stent comprises a swinging hook type of collapsing element, a removal tool such as a loop snare, wire basket stone extractor, stone forceps, or other device can also be used to grasp and withdraw the deployed stent. These types of devices are known in the art, available commercially, and described, for example, in U.S. Pat. No. 5,330,482. A basket retrieval device can be used to catch or engage the stent from its internal lumen. As described previously, when deployed in a target site, a removable stent can have a hinged hook collapsing element in a down position so as not to impede the fluid flow. In order to collapse the proximal end of the stent, the physician can position the hook(s) into an upright or up position. The resistive characteristics of the hinge portion of the hook maintains the collapsing element in the up position, allowing the physician to manipulate the wires of the basket retrieval device until they engage with the hooks. Retraction of the basket pulls on the collapsing element, which collapses the proximal end of the stent. The stent is withdrawn and removed from the patient.

The systems and methods of the present invention provide accurate, easy to use and stable grasping of a stent allowing for its safe removal from a target site in vivo. The features of the invention, as described herein, also provide a removable stent that is less awkward or cumbersome for the physician to use.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

All publications and patent applications in this specification are herein incorporated by reference to the same extent as if each individual publication or patent application was specifically and individually indicated by reference.

What is claimed is:

1. A method of removing a stent from a target site comprising:

providing a removable stent having an inner lumen, an outer surface, a collapsible end and a collapsing element, wherein at least a portion of said collapsing element contacts said outer surface of said removable stent;

maneuvering a tool toward said removable stent such that said tool engages said collapsing element;

compressing said collapsible open end of said removable stent through continued engagement of said collapsing element;

removing said removable stent from said target site;

wherein said tool is maneuvered within said inner lumen of said removable stent, and wherein said collapsing element comprises a lasso having a loop disposed within said inner lumen of said removable stent.

* * * * *